(12) United States Patent
Macht et al.

(10) Patent No.: US 9,169,188 B2
(45) Date of Patent: Oct. 27, 2015

(54) PROCESS FOR PREPARING AN UNSATURATED ALDEHYDE AND/OR AN UNSATURATED CARBOXYLIC ACID

(71) Applicant: BASF SE, Ludwigshafen (DE)

(72) Inventors: Josef Macht, Ludwigshafen (DE); Christian Walsdorff, Ludwigshafen (DE); Cornelia Katharina Dobner, Ludwigshafen (DE); Cathrin Alexandra Welker-Nieuwoudt, Birkenheide (DE); Ulrich Hammon, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/536,969

(22) Filed: Nov. 10, 2014

(65) Prior Publication Data

US 2015/0133687 A1    May 14, 2015

(30) Foreign Application Priority Data

Nov. 11, 2013  (EP) .................................... 13192279

(51) Int. Cl.

| | |
|---|---|
| C07C 51/16 | (2006.01) |
| C07C 51/42 | (2006.01) |
| C07C 51/25 | (2006.01) |
| B01J 23/887 | (2006.01) |
| C07C 45/35 | (2006.01) |

(52) U.S. Cl.
CPC ............ *C07C 51/252* (2013.01); *B01J 23/8876* (2013.01); *C07C 45/35* (2013.01)

(58) Field of Classification Search
None
See application file for complete search history.

(56) References Cited

U.S. PATENT DOCUMENTS

| | | |
|---|---|---|
| 4,538,874 A | 9/1985 | Dambach et al. |
| 4,656,157 A | 4/1987 | Hofmann et al. |
| 5,144,091 A | 9/1992 | Martan et al. |
| 5,449,821 A | 9/1995 | Neumann et al. |
| 5,583,086 A | 12/1996 | Tenten et al. |
| 5,739,391 A | 4/1998 | Ruppel et al. |
| 5,821,390 A | 10/1998 | Ruppel et al. |
| 6,333,011 B1 | 12/2001 | Schliephake et al. |
| 6,395,936 B1 | 5/2002 | Arnold et al. |
| 6,998,504 B1 * | 2/2006 | Unverricht et al. ........... 562/545 |
| 7,534,339 B2 | 5/2009 | Matsumoto et al. |
| 8,785,344 B2 | 7/2014 | Karpov et al. |
| 2004/0015013 A1 | 1/2004 | Hammon et al. |
| 2004/0034249 A1 | 2/2004 | Arnold et al. |
| 2004/0192965 A1 | 9/2004 | Petzoldt et al. |
| 2004/0242926 A1 | 12/2004 | Dieterle et al. |
| 2005/0038291 A1 | 2/2005 | Petzoldt et al. |
| 2005/0065371 A1 | 3/2005 | Petzoldt et al. |
| 2005/0131253 A1 | 6/2005 | Teshigahara et al. |
| 2007/0003076 A1 | 1/2007 | Croft, III |
| 2007/0032377 A1 | 2/2007 | Hibst et al. |
| 2008/0076838 A1 | 3/2008 | Puppe |
| 2008/0177105 A1 | 7/2008 | Raichle et al. |
| 2010/0010238 A1 | 1/2010 | Eger et al. |
| 2011/0065953 A1 | 3/2011 | Cremer et al. |
| 2011/0130596 A1 | 6/2011 | Macht et al. |
| 2014/0018572 A1 | 1/2014 | Welker-Nieuwoudt et al. |
| 2014/0221683 A1 | 8/2014 | Welker-Nieuwoudt et al. |
| 2014/0343319 A1 | 11/2014 | Goebel et al. |

FOREIGN PATENT DOCUMENTS

| | | |
|---|---|---|
| DE | 79219 | 1/1895 |
| DE | 33 38 380 C2 | 10/1988 |
| DE | 44 07 020 A1 | 9/1994 |
| DE | 44 31 957 A1 | 3/1995 |
| DE | 199 10 506 A1 | 9/2000 |
| DE | 100 46 957 A1 | 4/2002 |
| DE | 100 49 873 A1 | 4/2002 |
| DE | 10232748 | 7/2002 |
| DE | 103 36 386 A1 | 3/2004 |
| DE | 103 13 208 A1 | 10/2004 |
| DE | 103 13 213 A1 | 10/2004 |
| DE | 103 37 788 A1 | 10/2004 |
| DE | 10 2006 044 520 A1 | 4/2008 |
| DE | 10 2007 005 606 A1 | 4/2008 |
| DE | 10 2007 003 076 A1 | 7/2008 |
| DE | 10 2007 004 961 A1 | 7/2008 |
| DE | 10 2008 040 093 A1 | 12/2008 |
| DE | 10 2008 042 060 A1 | 6/2009 |
| DE | 10 2009 047 291 A1 | 9/2010 |
| DE | 10 2011 084 040 A1 | 1/2012 |
| EP | 0 184 790 A2 | 6/1986 |
| EP | 0 468 290 A1 | 1/1992 |
| EP | 0 575 897 A1 | 12/1993 |
| EP | 0 700 714 A1 | 3/1996 |
| EP | 0 700 893 A1 | 3/1996 |
| EP | 0 873 783 A1 | 10/1998 |
| EP | 1 106 598 A2 | 6/2001 |
| EP | 1 270 065 A1 | 1/2003 |
| EP | 1 547 994 A1 | 6/2005 |

(Continued)

OTHER PUBLICATIONS

U.S. Appl. No. 14/535,743, filed Nov. 7, 2014, Macht, et al.

*Primary Examiner* — Yevegeny Valenrod
(74) *Attorney, Agent, or Firm* — Oblon, McClelland, Maier & Neustadt, L.L.P.

(57) ABSTRACT

An $\alpha,\beta$-unsaturated aldehyde and/or an $\alpha,\beta$-unsaturated carboxylic acid are prepared by gas phase oxidation of alkene with molecular oxygen over a fixed catalyst bed comprising a bed of hollow cylindrical shaped catalyst bodies having a multimetal oxide active composition. The fixed catalyst bed comprises at least three successive reaction zones; the highest local temperature in the fixed catalyst bed does not occur in the reaction zone closest to the reactor outlet; the highest local temperature in the fixed catalyst bed does not occur in the reaction zone closest to the reactor inlet; and the value WT= (ED−ID)/2 in the reaction zone in which the highest local temperature in the fixed catalyst bed occurs is lower than in the other reaction zones, in which ED is the external diameter and ID is the internal diameter of the shaped catalyst body. The yield of the products of value is enhanced in this way.

22 Claims, No Drawings

(56) References Cited

FOREIGN PATENT DOCUMENTS

| | | |
|---|---|---|
| EP | 1 350 566 B1 | 1/2006 |
| EP | 1 526 123 B1 | 7/2008 |
| WO | WO 02/24620 A2 | 3/2002 |
| WO | WO 2005/030393 A1 | 4/2005 |
| WO | WO 2007/017431 A1 | 2/2007 |
| WO | WO 2007/082827 A1 | 7/2007 |
| WO | WO 2008/087116 A1 | 7/2008 |

* cited by examiner

PROCESS FOR PREPARING AN UNSATURATED ALDEHYDE AND/OR AN UNSATURATED CARBOXYLIC ACID

At present, the preparation of α,β-unsaturated aldehydes and/or α,β-unsaturated carboxylic acids on the industrial scale, especially of acrolein and acrylic acid, is effected essentially by heterogeneously catalyzed partial oxidation of alkenes (see, for example, DE-A 103 36 386 regarding preparation of acrylic acid by partial oxidation of propene).

The reaction is strongly exothermic, as a result of which a temperature profile characterized by a highest local temperature is established along the gas flow in the catalyst bed.

If this temperature is high, this is accompanied by increased oxidation. This results in a decrease in the yield of the products of value (of α,β-unsaturated aldehyde and α,β-unsaturated carboxylic acid).

At high temperatures, the catalyst is also deactivated more quickly. The deactivation is particularly marked in regions having particularly high temperature. The advancing deactivation of the catalyst also reduces the yield of the products of value.

The prior art has proposed processes for partial oxidation of alkenes to α,β-unsaturated aldehydes and α,β-unsaturated carboxylic acids with increased yield of product of value. One proposal has been that of structured catalyst beds along the flow direction of the gases.

EP 1 350 566 B1 discloses a process for preparing an unsaturated aldehyde and/or an unsaturated carboxylic acid by gas phase oxidation in a fixed-bed multitubular reactor. The particulate catalysts have a hole, the external diameter D1 being in the range from 3 to 15 mm and the diameter D2 of the hole being in the range from 0.1×D1 to 0.7×D1. The catalyst-packed layer of each reaction tube is divided into three reaction zones in tubular axial direction, the diameter of the hole in the second reaction zone being less than in the first reaction zone, and the external diameter in the third reaction zone being less than in the second reaction zone. The dimensions reported in mm (external diameter (ED)×height (H)×internal diameter (ID)) of the catalysts in examples 1-3 and 1-5 were 7.0×7.7×3.0 in the first reaction zone, 6.0×6.6×2.0 in the second reaction zone and 5.5×6.1×2.0 in the third reaction zone.

EP1526123B1 describes a catalytic gas phase oxidation reaction for production of an unsaturated aldehyde or an unsaturated carboxylic acid in a fixed-bed multitubular reactor. The catalyst-packed fixed bed comprises at least two reaction zones, the occupation volume, meaning the volume of the catalyst neglecting the void volumes, in a reaction zone closest to the gas outlet side being less than that in a reaction zone closest to the gas inlet side. In particular examples, 3 reaction zones with hollow cylindrical catalysts are used. In these examples, the dimensions of the catalyst in two immediately adjacent reaction zones in each case are the same.

In industrial scale processes, even small yield enhancements are worthwhile. It is therefore an object of the present invention to further enhance the yield of the products of value.

The object is achieved by a process for preparing an α,β-unsaturated aldehyde and/or an α,β-unsaturated carboxylic acid by gas phase oxidation of an alkene with molecular oxygen over a fixed catalyst bed comprising a bed of hollow cylindrical shaped catalyst bodies having a multimetal oxide active composition, wherein
(i) the fixed catalyst bed comprises at least three successive reaction zones;
(ii) the highest local temperature in the fixed catalyst bed does not occur in the reaction zone closest to the reactor outlet;
(iii) the highest local temperature in the fixed catalyst bed does not occur in the reaction zone closest to the reactor inlet; and
(iv) the value WT according to the following equation in that reaction zone in which the highest local temperature in the fixed catalyst bed occurs is lower than in the other reaction zones:

$$WT = \frac{ED - ID}{2}$$

in which ED is the external diameter and ID is the internal diameter of the shaped catalyst body.

The alkene is preferably selected from alkenes having 3 to 6, i.e. 3, 4, 5 or 6, carbon atoms; preferably selected from propene and isobutene. Propene is particularly preferred. Especially useful are polymer-grade propene and chemical-grade propene, as described, for example, by DE-A 102 32 748.

The process is particularly suitable for preparation of α,β-unsaturated aldehydes, especially for preparation by gas phase oxidation of propene, and of methacrolein by gas phase oxidation of isobutene. It is preferably a process for preparing acrolein by gas phase oxidation of propene.

In the process according the invention, hollow cylindrical shaped catalyst bodies are used, having a multimetal oxide active composition. Multimetal oxides for gas phase oxidation of alkenes to α,β-unsaturated aldehydes and/or α,β-unsaturated carboxylic acids are known per se. Therefore, a useful multimetal oxide is any capable of catalyzing this gas phase oxidation. Preferably, the active composition of the shaped catalyst bodies in the reaction zones is the same.

A reaction zone is understood to mean a coherent section of the bed which comprises shaped catalyst bodies and in which the composition of the bed is essentially homogeneous. In the bed, exclusively hollow cylindrical shaped catalyst bodies or else substantially homogeneous mixtures of hollow cylindrical shaped catalyst bodies and shaped diluent bodies are present. Within a reaction zone too, the bed is only approximately homogeneous, since the hollow cylindrical shaped catalyst bodies and any shaped diluent bodies in the reaction zone are generally aligned randomly and distributed statistically. The individual reaction zones differ from one another in at least one property selected from the content of inert shaped diluent bodies, form of the catalysts, space-filling level of the catalysts, active composition content of the catalysts and chemical composition of the active composition.

A non-monotonous temperature profile is established over the catalyst bed. There is development in the catalyst bed of local temperature maxima, called "hotspots", where the temperature is higher than in adjacent parts of the catalyst bed. The "highest local temperature in the fixed catalyst bed" is understood to mean the highest local temperature maximum in the entire fixed catalyst bed.

The geometry of the hollow cylindrical shaped catalyst bodies is characterized by the dimensions of external diameter (ED), height (H) and internal diameter (ID). The hollow cylindrical geometry of the present shaped catalyst bodies can be described by two cylinders of equal height and having coincident axes. One of the cylinders has a diameter ID. The other cylinder has a diameter ED. The outer surface of the inner cylinder coincides with the inner face of the hollow cylindrical shaped catalyst body. The outer surface of the outer cylinder coincides with the outer face of the hollow cylindrical shaped catalyst body.

The value WT corresponds to the wall thickness (WT) of the hollow cylindrical shaped catalyst bodies (equation 1).

$$WT = \frac{ED - ID}{2} \quad \text{(equation 1)}$$

In the process according to the invention, WT in that reaction zone in which the highest local temperature in the fixed catalyst bed occurs is smaller than in the other reaction zones.

In at least one reaction zone, preferably in all the reaction zones, shaped catalyst bodies having a geometric volume of preferably less than 120 mm$^3$, more preferably less than 80 mm$^3$, especially preferably less than 60 mm$^3$, are used. It can be calculated on the basis of the height H of the cylinder, the external diameter ED and the diameter of the inner bore ID. A hollow cylinder having the dimensions ED=4 mm, H=3 mm and ID=2 mm, for example, has a geometric volume of 28.27 mm$^3$.

In at least one reaction zone, preferably in all the reaction zones, shaped catalyst bodies having a ratio of geometric volume to geometric surface area of less than 0.9 mm, preferably less than 0.7 mm, more preferably less than 0.55 mm, are used. More preferably, the shaped catalyst bodies, at least in that reaction zone in which the highest local temperature in the fixed catalyst bed occurs, have a ratio of geometric volume to geometric surface area of less than 0.5 mm, preferably less than 0.45 mm, more preferably less than 0.4 mm.

The geometric surface area is an idealized parameter and does not take account of the increase in surface area caused by the porosity or surface roughness of the shaped body. The geometric surface area of hollow cylindrical shaped catalyst bodies is calculated by the following formula:

$$\frac{\pi}{2}((ED)^2 - (ID)^2) + \pi(ED + ID)H$$

Preferably, the volume-specific catalyst activity of that reaction zone in which the highest local temperature in the fixed catalyst bed occurs is lower than in the other reaction zones.

The (relative) volume-specific catalyst activity can be determined as the reaction rate of an individual reaction zone based on the catalyst bed volume. The (relative) volume-specific catalyst activity is determined using only one catalyst bed in each case, which reflects the composition of a reaction zone. The other reaction conditions, especially the control of the reactor temperature, the composition of the reaction gas and the space velocity on the bed, and also the bed length, are not varied in the determination of the volume-specific catalyst activity. The reaction rate, which is crucial for the determination of the (relative) volume-specific catalyst activity, is the rate at which the alkene is converted.

The volume-specific catalyst activity of a reaction zone can be varied by altering the catalyst active composition density. The catalyst active composition density is defined as the ratio of the weight of the active composition introduced into the respective reaction zone to the volume of the respective reaction zone.

Preferably, the catalyst active composition density of that reaction zone in which the highest local temperature of the fixed catalyst bed occurs is lower than in the other reaction zones.

The catalyst active composition density or the volume-specific catalyst activity of a reaction zone can be reduced by using a substantially homogeneous mixture of hollow cylindrical shaped catalyst bodies and shaped diluent bodies in the reaction zone. The higher the proportion of shaped diluent bodies selected, the lower the proportion of active composition present in the reaction zone.

The catalyst active composition density or the volume-specific catalyst activity can be reduced by using hollow cylindrical shaped catalyst bodies in which the active composition is in diluted form, diluted by finely divided inert dilution materials such as finely divided silicon carbide or finely divided silicates such as magnesium silicate and aluminum silicate or steatite. For instance, it is possible to mix a finely divided powder of an active composition with finely divided dilution material, and to shape the resulting mixed powder to a geometric shaped body using a shaping process (preferably by tableting).

The volume-specific catalyst activity can be reduced by using hollow cylindrical shaped catalyst bodies which have been calcined at elevated temperature and/or over a longer period in that reaction zone in which the highest local temperature in the fixed catalyst bed occurs.

The lower volume-specific catalyst activity is preferably achieved at least partly, especially preferably exclusively, through appropriate selection of the dimensions of the hollow cylindrical shaped catalyst bodies.

In one embodiment, the external diameter of the shaped catalyst bodies in that reaction zone in which the highest local temperature in the fixed catalyst bed occurs is less than the external diameter of the shaped catalyst bodies in the other reaction zones, and the internal diameter of the shaped catalyst bodies in all the reaction zones is the same.

In an alternative embodiment, the internal diameter of the shaped catalyst bodies in that reaction zone in which the highest local temperature in the fixed catalyst bed occurs is greater than the internal diameter of the shaped catalyst bodies in the other reaction zones, and the external diameter of the shaped catalyst bodies in all the reaction zones is the same.

Preferably, the fixed catalyst bed comprises three successive reaction zones, and (i) the first reaction zone has 70 to 90% of the volume-specific catalyst activity of the third reaction zone, and (ii) the second reaction zone has 50 to 70% of the volume-specific catalyst activity of the third reaction zone.

Preferably, the fixed catalyst bed comprises three successive reaction zones, and (i) the first reaction zone has 70 to 90% of the catalyst active composition density of the third reaction zone, and (ii) the second reaction zone has 50 to 70% of the catalyst active composition density of the third reaction zone.

Advantageous hollow cylindrical shaped bodies have a ratio of height to external diameter (H/ED) in the range from 0.4 to 0.9, preferably 0.45 to 0.85.

In general, the hollow cylindrical shaped catalyst bodies have an external diameter of 3 to 5 mm, a height of 2 to 4 mm and an internal diameter of 1 to 4 mm.

Preferably, the height of the shaped catalyst bodies in all the reaction zones is the same.

Preferably, the fixed catalyst bed comprises three successive reaction zones, and (i) the first reaction zone comprises shaped catalyst bodies having an external diameter of 5 mm, a height of 3 mm and an internal diameter of 2 mm, (ii) the second reaction zone comprises shaped catalyst bodies having an external diameter of 5 mm, a height of 3 mm and an internal diameter of 3 mm, and (iii) the third reaction zone comprises shaped catalyst bodies having an external diameter of 5 mm, a height of 3 mm and an internal diameter of 2 mm.

More preferably, the fixed catalyst bed comprises three successive reaction zones, and (i) the first reaction zone comprises shaped catalyst bodies having an external diameter of 5 mm, a height of 2.5 mm and an internal diameter of 2 mm, (ii) the second reaction zone comprises shaped catalyst bodies having an external diameter of 5 mm, a height of 2.5 mm and an internal diameter of 3 mm, and (iii) the third reaction zone comprises shaped catalyst bodies having an external diameter of 5 mm, a height of 2.5 mm and an internal diameter of 2 mm.

Preferably, the fixed catalyst bed comprises three successive reaction zones, and (i) the first reaction zone comprises shaped catalyst bodies having an external diameter of 5 mm, a height of 3 mm and an internal diameter of 2 mm, (ii) the second reaction zone comprises shaped catalyst bodies having an external diameter of 4 mm, a height of 3 mm and an internal diameter of 2 mm, and (iii) the third reaction zone comprises shaped catalyst bodies having an external diameter of 5 mm, a height of 3 mm and an internal diameter of 2 mm.

Preferably, the fixed catalyst bed comprises three successive reaction zones, and (i) the first reaction zone comprises shaped catalyst bodies having an external diameter of 5 mm, a height of 2.5 mm and an internal diameter of 2 mm, (ii) the second reaction zone comprises shaped catalyst bodies having an external diameter of 4 mm, a height of 2.5 mm and an internal diameter of 2 mm, and (iii) the third reaction zone comprises shaped catalyst bodies having an external diameter of 5 mm, a height of 2.5 mm and an internal diameter of 2 mm.

Either both of or, as described in EP-A 184790 or U.S. Pat. No. 4,656,157, only one of the end faces of the hollow cylindrical shaped catalyst bodies may be curved, for example in such a way that the radius of curvature is preferably 0.4 to 5 times the external diameter E. Preferably in accordance with the invention, neither of the end faces is curved.

Preferably, the fixed catalyst bed comprises three successive reaction zones, and (i) the first reaction zone makes up 2 to 5% of the volume of the fixed catalyst bed, (ii) the second reaction zone makes up 25 to 45% of the volume of the fixed catalyst bed, and (iii) the third reaction zone makes up 50 to 73% of the volume of the fixed catalyst bed.

The volume of the fixed catalyst bed is understood to mean the superficial volume occupied by the bed. It is calculated by multiplying the length of the fixed catalyst bed by the cross-sectional area thereof.

One or more reaction zones of the fixed catalyst bed may comprise mixtures of shaped catalyst bodies and inert material. The inert material is preferably in the form of shaped bodies. The geometry of these shaped diluent bodies may in principle be as desired. In other words, they may, for example, be spheres, polygons, solid cylinders or else hollow cylinders. More preferably, the inert material is in the form of hollow cylindrical shaped bodies having dimensions corresponding essentially to the external diameter, height and internal diameter of the shaped catalyst bodies used in the respective reaction zone. Preferably, the external diameter, height and internal diameter each differ by not more than 0 to 1 mm from the external diameter, height and internal diameter of the shaped catalyst bodies used in the respective reaction zone. Preference is given to using steatite as inert material.

The hollow cylindrical shaped catalyst bodies preferably consist predominantly of the multimetal oxide, especially to an extent of 80 to 100% by weight, further preferably to an extent of 85 to 100% by weight, more preferably to an extent of 90 to 100% by weight (so-called shaped unsupported catalyst bodies). In addition, shaping aids and/or finely divided inert diluent material may be present in the hollow cylindrical shaped catalyst bodies.

The shaping aids are especially reinforcers such as microfibers, for example of glass, asbestos, silicon carbide or potassium titanate, which have a beneficial effect on the integrity of the resulting shaped body after the shaping has ended. Other shaping aids, especially lubricants, for example graphite, carbon black, polyethylene glycol, polyacrylic acid, stearic acid, starch, mineral oil, vegetable oil, water, glycerol, cellulose ether, boron trifluoride and/or boron nitride, which can be added in the course of production of the shaped catalyst body, escape wholly or partly in the form of gaseous compounds (e.g. CO, $CO_2$), especially in the course of calcination.

Useful finely divided inert diluent materials include element oxides which have been calcined at high temperatures and have a comparatively low pore level as a result, such as aluminum oxide, silicon dioxide, thorium dioxide and zirconium dioxide. Other inert diluent materials which may be present in the shaped catalyst bodies include finely divided silicon carbide or finely divided silicates such as magnesium silicate and aluminum silicate, or steatite.

Also useful as hollow cylindrical shaped catalyst bodies are hollow cylindrical eggshell catalysts. The hollow cylindrical eggshell catalysts may comprise, for example, an active composition applied to inert hollow cylindrical shaped bodies.

The density of the shaped catalyst bodies is preferably 1.2 to 2.0 $g/cm^3$. It is calculated by dividing the mass of the shaped catalyst body by the geometric volume thereof.

Multimetal oxides for gas phase oxidation of alkenes to α,β-unsaturated aldehydes and/or α,β-unsaturated carboxylic acids are known per se. A suitable multimetal oxide is therefore any capable of catalyzing this gas phase oxidation. Preferably, the multimetal oxide comprises at least the elements iron, bismuth and at least one of the elements molybdenum and tungsten.

The multimetal oxide may correspond, for example, to the formula (I)

$$Mo_{12}Bi_aFe_bX^1_cX^2_dX^3_eX^4_fO_n \qquad (I)$$

in which
$X^1$ is nickel and/or cobalt,
$X^2$ is thallium, an alkali metal and/or an alkaline earth metal,
$X^3$ is zinc, phosphorus, arsenic, boron, antimony, tin, cerium, lead, vanadium, chromium and/or tungsten,
$X^4$ is silicon, aluminum, titanium and/or zirconium,
a is a number in the range from 0.2 to 5,
b is a number in the range from 0.01 to 10,
c is a number in the range from 0 to 10,
d is a number in the range from 0 to 2,
e is a number in the range from 0 to 8,
f is a number in the range from 0 to 10, and
n is a number which is determined by the valency and frequency of the elements other than oxygen in (I);
or correspond to the formula (II)

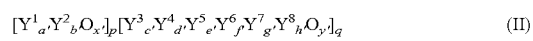

$$[Y^1_{a'}Y^2_{b'}O_{x'}]_p[Y^3_{c'}Y^4_{d'}Y^5_{e'}Y^6_{f'}Y^7_{g'}Y^8_{h'}O_{y'}]_q \qquad (II)$$

in which
$Y^1$ is bismuth or is bismuth and at least one of the elements tellurium, antimony, tin and copper,
$Y^2$ is molybdenum or tungsten, or is molybdenum and tungsten,
$Y^3$ is an alkali metal, thallium and/or samarium,
$Y^4$ is an alkaline earth metal, nickel, cobalt, manganese, zinc, tin, cadmium and/or mercury,
$Y^5$ is iron or is iron and at least one of the elements vanadium, chromium and cerium,
$Y^6$ is phosphorus, arsenic, boron, antimony and/or bismuth, $Y^7$ is a rare earth metal, titanium, zirconium, niobium, tantalum, rhenium, ruthenium, rhodium, copper, silver, gold, aluminum, gallium, indium, silicon, germanium, lead, thorium and/or uranium, $Y^8$ is molybdenum or tungsten, or is molybdenum and tungsten, a' is a number in the range from 0.01 to 8, b' is a number in the range from 0.1 to 30, c' is a number in the range from 0 to 4, d' is a number in the range from 0 to 20, e' is a number greater than 0 in the range from 0 to 20, f' is a number in the range from 0 to 6, g' is a number in the range from 0 to 15, h' is a number in the range from 8 to 16, x' and y' are numbers which are determined by the valency and frequency of the elements other than oxygen in (II), and p and q are numbers whose ratio p/q is 0.1 to 10.

In the formula (I), the stoichiometric coefficient b is preferably 2 to 4, the stoichiometric coefficient c is preferably 3 to 10, the stoichiometric coefficient d is preferably 0.02 to 2, the stoichiometric coefficient e is preferably 0 to 5 and the stoichiometric coefficient a is preferably 0.4 to 2. The stoichiometric coefficient f is advantageously 0.5 or 1 to 10. More preferably, the aforementioned stoichiometric coefficients are all within the preferred ranges mentioned.

In addition, $X^1$ is preferably cobalt, $X^2$ is preferably K, Cs and/or Sr, more preferably K, $X^3$ is preferably tungsten, zinc and/or phosphorus and $X^4$ is preferably Si. More preferably, the variables $X^1$ to $X^4$ all have the aforementioned definitions.

More preferably, all the stoichiometric coefficients a to f and all the variables $X^1$ to $X^4$ have their aforementioned advantageous definitions.

Within the stoichiometries of the formula (I) preference is given to those which correspond to the formula (Ia)

$$Mo_{12}Bi_aFe_bX^1_cX^2_dX^4_fO_n \quad (Ia)$$

in which $X^1$ is Co and/or Ni, $X^2$ is alkali metal, $X^4$ is Si and/or Al, a is a number in the range from 0.3 to 1, b is a number in the range from 0.5 to 10, c is a number in the range from 2 to 10, d is a number in the range from 0 to 0.5, f is a number in the range from 0 to 10, and n is a number which is determined by the valency and frequency of the elements other than oxygen in (Ia).

Preferably, in the crystalline components of the multimetal oxide of the formula (I), aside from β-$X^1MoO_4$ as the main component, $Fe_2(MoO_4)_3$ is present as a secondary component, and no $MoO_3$ is present.

Among the metal oxides of the formula (Ia), cobalt-containing multimetal oxides have been found to be particularly useful. In a particularly preferred embodiment, the multimetal oxide corresponds to the formula (Ia) in which $X^1$ is Co, $X^2$ is K, $X^4$ is Si, a is a number in the range from 0.5 to 1, b is a number in the range from 1.5 to 3, c is a number in the range from 7 to 8.5, d is a number in the range from 0 to 0.15, f is a number in the range from 0 to 2.5.

Preferably, the multimetal oxide of the formula (Ia) fulfills the following conditions 1, 2 and 3:

condition 1: 12−c−1.5·b=A where A is a number in the range from 0.5 to 1.5;

condition 2: the quotient a/A is a number in the range from 0.2 to 1.3;

condition 3: the quotient c/b is a number in the range from 2.5 to 9.

Preferably, the composition of the multimetal oxide (Ia) is $Mo_{12}Bi_{0.6}Fe_3Co_7K_{0.08}Si_{1.6}O_n$ and more preferably $Mo_{12}Bi_{0.6}Fe_{2.1}Co_{8.3}K_{0.08}Si_{1.6}O_n$.

In multimetal oxides of the formula (II), regions of the chemical composition $[Y^1_aY^2_bO_x]$ and regions of the chemical composition $[Y^3_cY^4_dY^5_eY^6_fY^7_gY^8_hO_y]$ are distributed relative to one another as in a mixture of finely divided $[Y^1_aY^2_bO_x]$ and finely divided $[Y^3_cY^4_dY^5_eY^6_fY^7_gY^8_hO_y]$.

Preference is given to multimetal oxides of the formula (II) comprising three-dimensional regions which differ from their local environment on the basis of their different composition than their local environment and are of the chemical composition $Y^1_aY^2_bO_x$, and which have a maximum diameter (longest connecting line passing through the center of the region between two points on the surface (interface) of the region) of 1 nm to 100 μm, frequently 10 nm to 500 nm or 1 μm to 50 or 25 μm.

In addition, it is advantageous when at least 25 mol % (preferably at least 50 mol % and more preferably 100 mol %) of the total proportion of $[Y^1_aY^2_bO_x]_p$ in the multimetal oxides of the stoichiometry (II) is present in the multimetal oxides of the stoichiometry (II) in the form of three-dimensional regions which differ from their local environment on the basis of their different chemical composition than their local environment and are of the chemical composition $Y^1_aY^2_bO_x$, and which have a maximum diameter in the range from 1 nm to 100 μm.

Advantageous multimetal oxides of the stoichiometry (II) are those in which $Y^1$ is bismuth alone. Among the multimetal oxides of the formula (II), preference is given to those which correspond to the formula (IIa)

$$[Bi_aY^2_bO_x]_p[Y^3_cY^4_dFe_eY^6_fY^7_gY^8_{12}O_y]_q \quad (IIa)$$

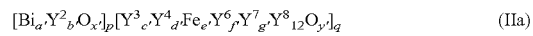

in which $Y^2$ is molybdenum or tungsten, or is molybdenum and tungsten, $Y^3$ is an alkali metal and/or thallium, preferably K, Cs, $Y^4$ is an alkaline earth metal, nickel, cobalt and/or tin, $Y^6$ is phosphorus, arsenic, boron, antimony and/or bismuth, $Y^7$ is titanium, zirconium, aluminum, silicon, copper, silver and/or gold, preferably Si, $Y^8$ is molybdenum or tungsten, or is molybdenum and tungsten, a' is a number in the range from 0.1 to 2, b' is a number in the range from 0.2 to 4, c' is a number in the range from 0.02 to 2, d' is a number in the range from 3 to 10, e' is a number in the range from 0.01 to 5, preferably 0.1 to 4, f' is a number in the range from 0 to 5, g' is a number in the range from 0 to 10, preferably a number greater than 0 in the range from 0 to 10, more preferably a number in the range from 0.2 to 10 and most preferably a number in the range from 0.4 to 3, x' and y' are numbers which are determined by the valency and frequency of the elements other than oxygen in (IIa), and p and q are numbers whose ratio p/q is 0.1 to 5, preferably 0.4 to 2.

Among the multimetal oxides of the formula (IIa), preference is given to those in which $Y^2$ is tungsten and $Y^8$ is molybdenum.

Preference is further given to multimetal oxides of the stoichiometry (IIa) comprising three-dimensional regions which differ from their local environment on the basis of their different composition than their local environment and are of the chemical composition $Bi_{a'}Y^2_{b'}O_{x'}$, and which have a maximum diameter (longest connecting line passing through the center of the region between two points on the surface (interface) of the region) of 1 nm to 100 µm, frequently 10 nm to 500 nm or 1 µm to 50 or 25 µm.

Correspondingly, it is advantageous when at least 25 mol % (preferably at least 50 mol % and more preferably 100 mol %) of the total proportion of $[Bi_aY^2_bO_x]_p$ in the multimetal oxides of the stoichiometry (IIa) is present in the multimetal oxides of the stoichiometry (IIa) in the form of three-dimensional regions which differ from their local environment on the basis of their different chemical composition than their local environment and are of the chemical composition $[Bi_{a'}Y^2_{b'}O_{x'}]$, and which have a maximum diameter in the range of 1 nm to 100 µm.

The composition of the multimetal oxide (IIa) is preferably $[Bi_1W_2O_{x'}]_{0.5}[K_{0.08}Co_{5.5}Fe_3Si_{1.6}Mo_{12}O_{y'}]$ and more preferably $[Bi_1W_2O_{x'}]_{0.4}[K_{0.08}Co_{5.5}Fe_3Si_{1.6}Mo_{12}O_{y'}]$.

It is preferably a feature of the multimetal oxide that it has essentially no local centers of element oxides (e.g. iron oxide). Instead, these elements are very substantially part of complex, mixed oxomolybdates. This reduces the unwanted full combustion of organic reaction gas constituents.

The multimetal oxide can be produced by using suitable sources of the elemental constituents thereof (especially other than oxygen) to produce a preferably finely divided intimate dry mixture of a composition corresponding to the particular stoichiometry, and, optionally after shaping to give hollow cylindrical shaped bodies, which is optionally effected with use of shaping aids, calcining the latter at temperatures in the range from 350 to 650° C. The term "source" in this document refers to a starting material for preparation of the multimetal oxide. The calcination can be effected either under inert gas or under an oxidative atmosphere, for example air (or another mixture of inert gas and molecular oxygen), or else under a reducing atmosphere (e.g. a mixture of inert gas, $NH_3$, CO and/or $H_2$) or under reduced pressure. The calcination time may be a few minutes to a few hours and typically decreases with the calcination temperature.

Useful sources include those compounds which are already oxides of metals present in the metal oxide and/or those compounds convertible to oxides by heating, at least in the presence of oxygen.

As well as the oxides, useful sources are particularly halides, nitrates, formates, oxalates, citrates, acetates, carbonates, amine complexes, ammonium salts and/or hydroxides of metals present in the metal oxide, and hydrates of the aforementioned salts. Compounds such as $NH_4OH$, $(NH_4)CO_3$, $NH_4NO_3$, $NH_4CHO_2$, $CH_3COOH$, $NH_4CH_3CO_2$ and/or ammonium oxalate, which can be broken down and/or decomposed to compounds which escape in gaseous form in the later calcination at the latest, can additionally be incorporated into the intimate dry mixture. Useful substances of this kind, which decompose in the course of calcination, also include organic materials, for example stearic acid, malonic acid, ammonium salts of the aforementioned acids, starches (e.g. potato starch and corn starch), cellulose, ground nutshells and finely ground polymer (e.g. polyethylene, polypropylene etc.).

The intimate mixing of the sources for preparation of the multimetal oxide can be effected in dry form or in wet form. If it is effected in dry form, the sources are appropriately used in the form of fine powders. However, the intimate mixing is preferably effected in wet form.

Advantageously in accordance with the invention, the sources are mixed with one another in the form of solutions and/or suspensions, and the resulting wet mixture is then dried to give an intimate dry mixture. The solvent and/or suspension medium used is preferably water or an aqueous solution.

Particularly intimate dry mixtures are obtained in the above-described mixing process when the starting materials are exclusively sources in dissolved form and/or colloidally dissolved sources of the elemental constituents. Generally, a starting compound may be a source for only one or for more than one of the elemental constituents. Correspondingly, any above-listed source in dissolved form or in colloidal form may have only one or else more than one of the elemental constituents. The drying of the resulting wet mixtures is preferably effected by spray-drying.

The element silicon can be introduced, for example, in the form of a silica sol for production of the wet mixture. Silica sols are colloidal solutions of amorphous silica in water. They have the fluidity of water and do not comprise any sedimentable constituents. The $SiO_2$ content thereof may be up to 50% by weight or more, often over a shelf life of several years (without sedimentation).

A source may also be partly dissolved and partly in colloidal form.

A favorable Mo source is ammonium heptamolybdate tetrahydrate. Further possible Mo sources are ammonium orthomolybdate ($(NH_4)_2MoO_4$), ammonium dimolybdate ($(NH_4)_2Mo_2O_7$), ammonium tetramolybdate dihydrate ($(NH_4)_2Mo_4O_{13}\times5H_2O$) and ammonium decamolybdate dihydrate ($(NH_4)_4Mo_{10}O_{32}\times2\,H_2O$). In principle, however, it is also possible to use molybdenum trioxide, for example.

A preferred K source is KOH (potassium hydroxide). In principle, however, it is also possible to use $KNO_3$ or the hydrate thereof as the K source.

Preferred Bi sources have the Bi in the form of $Bi^{3+}$. Useful Bi sources include, for example, bismuth(III) oxide, bismuth (III)oxide nitrate (bismuth subnitrate), bismuth(III) halide (e.g. fluoride, chloride, bromide, iodide) and especially bismuth(III) nitrate pentahydrate. Particular preference is given to using aqueous solutions of bismuth nitrate in nitric acid.

Preferred Fe sources are salts of $Fe^{3+}$, among which particular preference is given to iron(III)nitrate hydrates (cf., for example, DE-A 102007003076). A particularly preferred Fe source is iron(III) nitrate nonahydrate. It is of course also possible to use salts of $Fe^{2+}$ as the Fe source.

To prepare the multimetal oxide, based on the total molar proportion of Fe present therein, at least 50 mol %, better at least 75 mol % and preferably at least 95 mol % is introduced in the form of an Fe source which has the Fe as $Fe^{3+}$. It is also possible to use Fe sources having both $Fe^{2+}$ and $Fe^{3+}$.

Suitable Co sources are the salts thereof having the Co as $Co^{2+}$ and/or $Co^{3+}$. Examples of these include cobalt(II) nitrate hexahydrate, $Co_3O_4$, CoO, cobalt(II) formate and cobalt(III) nitrate. Cobalt(II) nitrate hexahydrate is preferred. Particular preference is given to using aqueous solutions of cobalt nitrate in nitric acid solution.

In general, the production of the wet mixture is preferably effected under air (advantageously, the wet mixture is air-saturated). This is especially true when the Co source used and the Fe source used are salts of $Co^{2+}$ and salts of $Fe^{2+}$. This is particularly true when these salts are the nitrates and/or hydrates thereof.

The intimate mixing of the sources for production of the multimetal oxide is preferably effected in wet form, more preferably in aqueous form. In this case, preferably at least one source of the elements Co, Fe and Bi is used to produce an aqueous solution A. Preferably, the aqueous solution A is an aqueous solution of the nitrates or nitrate hydrates of Co, Bi and Fe. More preferably, the aqueous solution A is an aqueous solution of the nitrates or nitrate hydrates in aqueous nitric acid. Such a solution can also be obtained by dissolving the corresponding metals in aqueous nitric acid.

At least one source of the element Mo and optionally one or more sources of the element K are used to produce an aqueous solution B.

A preferred Mo source for preparation of an aqueous solution B is ammonium heptamolybdate tetrahydrate ($(NH_4)_6Mo_7O_{24} \times 4H_2O$). If the aqueous solution B comprises K, the source thereof used for preparation of aqueous solution B is advantageously KOH.

The total Co, Fe and Bi content in the aqueous solution A is appropriately, based on the amount of water present in the aqueous solution A, 10 to 25% by weight, advantageously 15 to 20% by weight.

The total Mo content in the aqueous solution B is appropriately, based on the amount of water present in the aqueous solution B, 3 to 25% by weight, advantageously 5 to 15% by weight.

Preferably, the aqueous solution A and the aqueous solution B are mixed with one another. The procedure here is advantageously to stir the aqueous solution A continuously into the aqueous solution B, preferably with vigorous stirring of the initially charged aqueous solution B. The total Mo, Co, Fe and Bi content of the resulting wet mixture of aqueous solution A and aqueous solution B is appropriately, based on the amount of water present in the wet mixture, 5 to 25% by weight, preferably 8 to 20% by weight.

More particularly, for preparation of active compositions of the stoichiometry of the general formula II or IIa, it is advantageous to preform a mixed oxide $Y^1_a Y^2_b O_{x'}$ or $Bi_a Y^2_b O_{x'}$ as a source of the elements $Y^1$, $Y^2$ or Bi, $Y^2$ in the absence of the other constituents of the multimetal oxide. After the preformation, the mixed oxide is combined with sources of the other constituents of the multimetal oxide and the intimate dry mixture is produced therefrom. If the mixed oxide comes into contact with solvent, especially with water, in the course of production of the intimate dry mixture, it is preferable to ensure that the mixed oxide $Y^1_a Y^2_b O_{x'}$ or $Bi_a Y^2_b O_{x'}$ does not go into solution to a significant extent. A method of production as described above is described in detail in the documents DE-A 4407020, EP-A 835, EP-A 575897 and DE-C 3338380.

If the multimetal oxide comprises the elemental constituents Si, the source used therefor is advantageously aqueous silica sol (cf., for example, DE-A 102006044520), and the latter is advantageously stirred into the wet mixture, it being possible to add water to the wet mixture beforehand. Aqueous silica sol and water are preferably added simultaneously.

In the course of spray-drying of the wet mixture, it is first divided into fine droplets, and the fine droplets are then dried. Preference is given to spray-drying in a hot air stream. In principle, it is also possible to use other hot gases for spray-drying (e.g. nitrogen or nitrogen-diluted air, or else other inert gases).

This spray-drying can be effected either in a cocurrent or in countercurrent flow of the droplets relative to the hot gas. Typical gas inlet temperatures are in the range from 250 to 450° C., preferably 270 to 370° C. Typical gas outlet temperatures are in the range from 100 to 160° C. The spray-drying is preferably effected in a cocurrent flow of the droplets relative to the hot gas.

The wet mixture can also be dried by conventional evaporative concentration (preferably under reduced pressure; the drying temperature will generally not exceed 150° C.). In principle, the wet mixture can also be dried by freeze-drying.

Intimate dry mixture obtained by spray-drying is also referred to hereinafter as spray powder.

In principle, the intimate dry mixture can be calcined as such. Frequently, however, the spray powder is too finely divided for direct calcination.

The spray powder can be coarsened by subsequent compaction (generally to a particle size of 100 µm to 1 mm). Subsequently, the coarsened powder can be used to shape the hollow cylindrical shaped body, preceded by another addition of finely divided lubricant if required. Such a compaction for the purpose of particle coarsening can be effected, for example, by means of a compactor from Hosokawa Bepex GmbH (D-74211 Leingarten), of the K 200/100 compactor type.

In order to achieve a high mechanical stability of the hollow cylindrical shaped catalyst body, the compaction is controlled such that the coarsened powder particles obtained have a bulk density well below the target density of the shaped, uncalcined hollow cylindrical shaped body. In other words, further compaction of the coarsened powder particles is effected in the course of shaping, for example by tableting.

If the compaction is effected under dry conditions, the compaction may be preceded by mixing, for example, of finely divided graphite and/or other shaping aids mentioned in this document (e.g. lubricants and/or reinforcers) with the spray powder (for example with a drum-hoop mixer). For example, the compaction can be conducted with a calender having two contra-rotating steel rollers. Subsequently, the compactate can be comminuted, specifically to the particle size appropriate for the envisaged further use, to give a finely divided precursor material. This can be effected, for example, by forcing the compactate through a screen having defined mesh size.

Compaction can in principle also be effected under moist conditions. For example, the spray powder can be kneaded with addition of water. After the kneading, the kneaded mass, in accordance with the subsequent use, can be comminuted again to the desired level of fineness (cf., for example, DE-A 10049873) and dried to give a finely divided precursor material.

The finely divided precursor materials obtainable as described can then be calcined as such, or first shaped to hollow cylindrical shaped bodies and then calcined.

If the finely divided precursor material is calcined as such, it is then possible to produce a hollow cylindrical shaped catalyst body by shaping it to the hollow cylindrical form (for example by tableting or extruding), with optional addition of shaping aids such as lubricants and/or reinforcers. Preferred lubricants are graphite or stearic acid. Preferred reinforcers are microfibers of glass, asbestos, silicon carbide or potassium titanate.

Preferably, the intimate dry mixture, preferably the spray powder, is shaped by compaction to hollow cylindrical shaped precursor bodies, and the hollow cylindrical shaped precursor bodies are converted by calcination to the hollow cylindrical shaped catalyst bodies.

This procedure is preferred especially when the intimate mixing of the sources of the elemental constituents of the multimetal oxide to give the finely divided intimate dry mixture is effected in wet form (cf., for example, WO 2008/087116 and DE-A 102008042060).

Shaping aids which may be added include, for example, lubricants, for example graphite, carbon black, polyethylene glycol, polyacrylic acid, stearic acid, starch, mineral oil, vegetable oil, water, glycerol, cellulose ether, boron trifluoride and/or boron nitride. Further useful shaping aids include reinforcers such as microfibers of glass, asbestos, silicon carbide or potassium titanate, which, after the shaping by compaction has ended, have a beneficial effect on the integrity of the resulting shaped body. Use of lubricants in the context of a corresponding shaping operation can be found, for example, in documents DE-A 102007004961, WO 2008/087116, WO 2005/030393, US-A 2005/0131253, WO 2007/017431, DE-A 102007005606 and in DE-A 102008040093.

Preferably, exclusively finely divided graphite is used as a lubricant. Useful finely divided graphites for use are especially those recommended in documents WO 2005/030393, US-A 2005/0131253, WO 2008/087116 and DE-A 102007005606. This is especially true of those graphites which are used in the examples and comparative examples in these documents. Very particularly preferred graphites are Asbury 3160 and Asbury 4012 from Asbury Graphite Mills, Inc., New Jersey 08802, USA and Timrex® T44 from Timcal Ltd., 6743 Bodio, Switzerland.

Based on the weight of the intimate dry mixture, it may comprise, for example, up to 15% by weight of finely divided lubricant (e.g. graphite). Usually, the lubricant content, however, is not more than 9% by weight, in many cases not more than 5% by weight, often not more than 4% by weight, especially when the finely divided lubricant is graphite. In general, the aforementioned added amount is at least 0.5% by weight, usually at least 2.5% by weight.

In general, the shaping to give the hollow cylindrical shaped precursor body is effected by reaction of outside forces (pressure) on the dry mixture. The shaping apparatus to be employed, and the shaping method to be employed, are not subject to any restriction.

For example, the shaping can be effected by extrusion or tableting. This is preferably done using the intimate dry mixture when it is dry to the touch. It may, however, comprise, for example, up to 10% of its total weight of substances which are liquid under standard conditions (25° C., 1 atm (1.01 bar)). The intimate dry mixture may also comprise solid solvates (e.g. hydrates) including such liquid substances in chemically and/or physically bound form. The intimate dry mixture may also be entirely free of such substances.

The preferred shaping process is tableting. The principles of tableting are described, for example, in "Die Tablette", Handbuch der Entwicklung, Herstellung and Qualitätssicherung ["The Tablet", Handbook of Development, Production and Quality Assurance], W. A. Ritschel and A. Bauer-Brandl, 2nd edition, Edition Verlag Aulendorf, 2002, and are applicable to the tableting of the intimate dry mixture.

An example of a useful apparatus for the shaping to give the hollow cylindrical shaped catalyst precursor body is a Kilian RX 73 or S 100 rotary tableting press (from Kilian in D-50735 Cologne). Alternatively, it is possible to use a Korsch PH 800-65 tableting press (D-13509 Berlin).

In the course of tableting, the ambient temperature for the tableting machine is normally 25° C. Appropriately in application terms, the particle diameter of the intimate dry mixture, optionally as a result of a pre-coarsening operation by compaction, is in the range of 100 to 2000 μm, preferably 150 to 1500 μm, more preferably 400 to 1250 μm, or 400 to 1000 μm, or 400 to 800 μm (shaping aid mixed in prior to the compaction is not taken into account here). The shaping pressures are advantageously 50 to 5000 kg/cm², preferably 200 to 3500 kg/cm², more preferably 600 to 2500 kg/cm².

The hollow cylindrical shaped precursor bodies preferably have a minimum residual moisture content.

Preferably, the residual moisture content of the hollow cylindrical shaped precursor bodies is not more than 10% by weight, better not more than 8% by weight, even better not more than 6% by weight, and at best not more than 4% by weight or not more than 2% by weight (the residual moisture content can be determined as described in "Die Bibliothek der Technik" ["Library of Technology"], volume 229, "Thermogravimetrische Materialfeuchtebestimmung", Grundlagen und praktische Anwendungen ["Thermogravimetric Material Moisture Content Determination", Principles and Practical Applications], Horst Nagel, moderne Industrie publishers (for example with the aid of a Computrac MAX 5000 XL from Arizona Instruments)).

Against this background, spray-drying of the wet mixture should be conducted in such a way that the resulting spray powder has a minimum residual moisture content.

Hollow cylindrical shaped precursor bodies should as far as possible be stored with exclusion of ambient air (having air humidity) (storage until calcination is preferably effected under anhydrous inert gas or under air which has been dried beforehand).

Advantageously, the shaping of the intimate dry mixture is conducted with exclusion of ambient air (having air humidity) (for example under $N_2$ atmosphere).

The calcination of the hollow cylindrical shaped bodies (or generally of uncalcined finely divided precursor material or shaped support bodies coated therewith) is effected normally at temperatures which reach or generally exceed at least 350° C. Normally, in the course of calcination, the temperature of 650° C., however, is not exceeded (the term "calcination temperature" in this document means the temperature present in the calcination material). Preferably, in the course of calcination, the temperature of 600° C., preferably the temperature of 550° C. and frequently the temperature of 500° C. is not exceeded. In addition, in the course of the above calcination, preferably the temperature of 380° C., advantageously the temperature of 400° C., particularly advantageously the temperature of 420° C. and most preferably the temperature of 440° C. is exceeded.

The calcination period can also be divided into several sections. Preferred temperature windows for final calcination temperature are within the temperature range from 400° C. to 600° C., preferably 420 to 550° C., more preferably 440 to 500° C.

The calcination time is generally not more than 10 h. Usually, the duration of 45 h, or 25 h, is not exceeded. The duration is often below 20 h. In principle, a shorter calcination is generally effected at higher calcination temperatures than at lower calcination temperatures.

The calcination time within the temperature range from 430° C. to 500° C. preferably extends to 10 to 20 h.

Preferably, the calcination is preceded by an often stepwise thermal pretreatment at temperatures in the range from 110° C. to 350° C., preferably 120° C. to 320° C., more preferably 130° C. to 290° C. Such a thermal pretreatment is appropriately conducted until the constituents which break down to gaseous compounds under the conditions of the thermal pretreatment have substantially (preferably completely) been decomposed to gaseous compounds (the time required for this may, for example, be 3 h to 10 h, frequently 4 h to 8 h).

The duration and the temperature range for the thermal pretreatment are preferably selected such that the maximum relative change in mass which is established, based on the mass of the shaped catalyst precursor body, does not exceed a value of 1% per minute, in order to reliably avoid significant impairment of the mechanical shaped catalyst body stability resulting, for example, from crack formation by the decomposition gases which form in the shaped catalyst precursor body.

Both the calcination and the thermal pretreatment which precedes the calcination can be effected either under inert gas or under an oxidative atmosphere, for example air (or a mixture of inert gas and molecular oxygen), or else under reducing atmosphere (e.g. a mixture of inert gas, $NH_3$, CO and/or $H_2$ or under methane, acrolein, methacrolein). The calcination and/or the thermal treatment can also be performed under reduced pressure. The atmosphere can also be varied over the course of the calcination and/or the thermal pretreatment.

Preferably, the calcination and optionally also the thermal pretreatment which precedes the calcination are effected in an oxidizing atmosphere. Appropriately, this consists predominantly of stationary or (preferably) moving air (more preferably, an air stream flows through the calcination material). However, the oxidizing atmosphere may likewise consist of a stationary or moving mixture of, for example, 25% by volume of $N_2$ and 75% by volume of air, or 50% by volume of $N_2$ and 50% by volume of air, or 75% by volume of $N_2$ and 25% by volume of air (an atmosphere of 100% by volume of $N_2$ is likewise possible).

In principle, the calcination and optionally also the thermal pretreatment which precedes the calcination can be conducted in a wide variety of oven types, for example heatable air circulation chambers (air circulation ovens, e.g. air circulation shaft ovens), staged ovens, rotary tube ovens, belt calciners or shaft ovens. Preference is given to using a belt calcining apparatus as recommended by DE-A 10046957 and WO 02/24620. Hotspot formation within the calcination material is very substantially avoided by virtue of elevated volume flow rates of calcination atmosphere being conveyed through the calcination material on a gas-permeable conveyor belt which bears the calcination material with the aid of ventilators.

In the course of calcination and optionally also in the course of the thermal pretreatment which precedes the calcination, shaping aids may be conserved or converted to gaseous compounds which escape (e.g. CO, $CO_2$).

The calcined multimetal oxide can be ground to a finely divided powder, which can be mixed with finely divided inert diluent material, and the mixed powder thus obtained can be shaped to a hollow cylindrical shaped body by employing a shaping process presented in this document (preferably by tableting). By subsequently calcining this shaped body once again, the hollow cylindrical shaped catalyst body is then obtained.

The finely divided inert diluent material can alternatively also be incorporated into the wet mixture prior to the drying thereof. In addition, finely divided inert diluent material can be incorporated into a finely divided dry mixture of sources of the elemental constituents of the multimetal oxide. However, such procedures are less preferred.

The specific surface area of the hollow cylindrical shaped catalyst bodies is advantageously 2 to 20 or 15 $m^2/g$, preferably 3 to 10 $m^2/g$ and more preferably 4 to 8 $m^2/g$. The total pore volume is advantageously within the range from 0.1 to 1 $cm^3/g$ or to 0.8 $cm^3/g$, preferably within the range of 0.1 to 0.5 $cm^3/g$ and more preferably within the range of 0.2 to 0.4 $cm^3/g$.

All figures in this document for specific surface areas of solids relate to determinations to DIN 66131 (Determination of specific surface area of solids by gas adsorption using the method of Brunauer, Emmett and Teller (BET)), unless explicitly mentioned otherwise.

Preferably, the contribution of pores having a pore radius of not more than 0.1 μm to the total pore volume is not more than 0.05 $cm^3/g$. If the contribution of such comparatively narrow pores to the total pore volume is more than 0.05 $cm^3/g$, an increase in the calcination time and/or the calcination temperature can bring about an advantageous reduction in this contribution.

Preferably, the contribution of pores having a radius in the range from 0.2 to 0.4 μm to the total pore volume, based on the total pore volume, is at least 70% by volume, advantageously at least 75% by volume, particularly advantageously at least 85% by volume.

All figures in this document relating to total pore volumes and to pore diameter distributions for these total pore volumes are based on determinations by the method of mercury porosimetry using the Auto Pore 9500 instrument from Micromeritics GmbH, D-41238 Moenchengladbach (range 0.003-300 μm).

The hollow cylindrical shaped catalyst bodies have a high fracture stability in the course of reactor filling. The side crushing strength of the hollow cylindrical shaped catalyst bodies is generally 5 to 15 N, preferably 6 to 13 N, more preferably 8 to 11 N. The experimental determination of the side crushing strength is conducted as described in the documents WO 2005/030393 and WO 2007/017431.

The calcined shaped catalyst bodies are preferably stored in 120 l metal drums lined with a flat Lupolen sack having a material thickness of 0.1 mm.

The molecular oxygen and the alkene are contacted with the fixed catalyst bed by conducting the molecular oxygen and the alkene over the fixed catalyst bed. Preferably, a reaction gas comprising the molecular oxygen and alkene is conducted over the fixed catalyst bed and thus converted to a product gas.

The molecular oxygen is preferably supplied to the process in the form of air.

The proportion of the alkene present in the reaction gas will generally be 4 to 20% by volume, preferably 5 to 15% by volume, more preferably 5 to 12% by volume, especially preferably 5 to 8% by volume, based in each case on the reaction gas.

Preferably, the reaction gas also comprises at least one inert diluent gas. Inert diluent gases are understood to mean those gases which remain chemically unchanged in the course of the gas phase oxidation to an extent of at least 95 mol %, preferably to an extent of at least 98 mol %. Examples of inert diluent gases are $N_2$, $CO_2$, $H_2O$ and noble gases such as Ar, and mixtures of the aforementioned gases. The inert diluent gas used is preferably molecular nitrogen. The inert diluent gas may comprise, for example, at least 20% by volume, preferably at least 40% by volume, more preferably at least 60% by volume, especially preferably at least 80% by volume and most preferably at least 95% by volume of molecular nitrogen.

Preferably, cycle gas is used as a reaction gas constituent. Cycle gas is understood to mean the residual gas which remains when α,β-unsaturated aldehyde and/or α,β-unsaturated carboxylic acid is removed essentially selectively from the product gas of the gas phase oxidation. In this context, it should be taken into account that the process according to the invention may only be the first stage of a two-stage gas phase oxidation to give the α,β-unsaturated carboxylic acid as the actual target compound, such that the cycle gas is then usually formed only after the second stage. In such a two-stage gas phase oxidation, the product gas of the first stage, optionally after cooling and/or secondary oxygen addition (generally in the form of air), is generally sent to the second gas phase oxidation.

The reaction gas may also comprise at least one further gas constituent. The further gas constituent is preferably selected from CO, methane, ethane, propane, butane, pentane and $H_2$.

The reaction gas preferably comprises alkene:molecular oxygen:inert diluent gas in a volume ratio of 1:(1.0 to 3.0):(5 to 25), preferably 1:(1.5 to 2.3):(10 to 20).

In general, the space velocity of propene present in the reaction gas toward the bed is at least 90 l (STP)/(lh). Preferably, the space velocity of propene present in the reaction gas toward the bed is at least 100 l (STP)/(lh), preferably at least 130 l (STP)/(lh) in the case of one temperature zone, preferably at least 160 l (STP)/(lh) in the case of two temperature zones. Preferably, the space velocity of propene present in the reaction gas toward the bed is not more than 500, more preferably not more than 400, further preferably not more than 300 and especially preferably not more than 250 l (STP)/(lh). Space velocities in the range from 100 to 300 l (STP)/(lh), preferably 160 to 300 l (STP)/(lh) in the case of a plurality of temperature zones, or preferably 100 to 150 l (STP)/(lh) in the case of one temperature zone, are particularly appropriate. In this document, the space velocity of propene present in the reaction gas toward the bed is understood to mean the amount of propene present in reaction gas in standard liters (=l (STP); the volume in liters that the corresponding amount of propene would occupy under standard conditions, i.e. at 0° C. and 1 atm (1.01 bar)) which is supplied per liter of bed per hour (unit: l (STP)/(lh)). Upstream and/or downstream beds of inert material are not counted as part of the bed in space velocity considerations in this document; in other words, the volume of the bed is the volume of the bed comprising the hollow cylindrical shaped catalyst bodies.

In general, a total pressure of 0.5 to 4 bar, preferably of 1.5 to 3 bar, exists in the reaction gas. All pressure figures in this document relate to absolute pressures.

The process can be conducted, for example, in a fixed bed reactor having multiple catalyst tubes and one temperature zone, as described, for example, by DE-A 44 31 957, EP-A 700 714 and EP-A 700 893. In such a reactor, a fixed catalyst bed divided between the catalyst tubes is present. Typically, the catalyst tubes in the aforementioned reactors are manufactured from ferritic steel and typically have a wall thickness of 1 to 3 mm. The internal diameter thereof is generally 20 to 30 mm, frequently 21 to 26 mm. A typical catalyst tube length runs, for example, to 3.20 m.

Preferably, the number of catalyst tubes accommodated in the shell and tube vessel runs to at least 1000, preferably to at least 5000. Frequently, the number of catalyst tubes accommodated in the reaction vessel is 15 000 to 35 000. Shell and tube reactors having a number of catalyst tubes above 40 000 tend to be uncommon. Within the vessel, the catalyst tubes are normally arranged in homogeneous distribution, in which case the distribution is appropriately selected such that the distance between the central internal axes of mutually adjacent catalyst tubes (called the catalyst tube pitch) is 35 to 45 mm (cf. EP-B 468 290).

The process can also be conducted in a fixed bed reactor having multiple catalyst tubes and several temperature zones, as recommended by DE-A 199 10 506, DE-A 103 13 213, DE-A 103 13 208 and EP-A 1 106 598. A typical catalyst tube length in the case of a fixed bed reactor having multiple catalyst tubes and two temperature zones is 3.50 m. Everything else is essentially as in the fixed bed reactor having multiple catalyst tubes and one temperature zone.

To determine the temperature profile along the fixed catalyst bed in a reaction tube of a shell and tube reactor, it may have a thermowell which runs from the top downward through the center of the reaction tube, in which the temperature can be determined over the entire reaction tube length with the aid of thermocouples run through the thermowell. In principle, any reaction tube present within a shell and tube reactor and charged with the fixed catalyst bed could be modified as described above.

Appropriately in application terms, a shell and tube reactor, however, has only a limited number of thermal reaction tubes of this kind, or else merely "thermal tubes" for short (cf., for example, page 56 of WO 2007/082827, EP-A 873783, EP-A 1270065 and U.S. Pat. No. 7,534,339 B2).

Since thermal tubes, in addition to the fixed catalyst bed, also have to accommodate the thermowells, given otherwise identical tube configuration, they would have an equal heat exchange surface area but a lower free cross section which can be occupied by the fixed catalyst bed than a mere "reaction tube". This is taken into account by configuring them (the thermal tubes) such that the ratio of free cross-sectional area in the tube to the circumference of the tube is the same for thermal tube and reaction tube. Otherwise, reaction tube and thermal tube, given identical tube length, each have the same fixed catalyst bed structure over their tube length. When charging with fixed catalyst bed, it should additionally be ensured that the pressure drop profile established in each case over the tube length in the course of flow of reaction gas mixture through reaction tube or thermal tube is uniform in both tube types. Influence can be exerted in a corresponding manner via the rate of filling of the tubes with the shaped bodies and/or through additional use of comminuted (spalled) shaped bodies (cf., for example, EP-A 873783 and U.S. Pat. No. 7,534,339 B2). Overall, it is ensured in this way that a thermal tube and a reaction tube have equal ratios of evolution of heat of reaction in the tube interior and of removal of heat of reaction from the tube interior along the entire tube length. The thermal tube is thus capable of representing the profile of the temperature in the reaction tube for many reaction tubes.

The temperatures measured in the thermal tubes can thus be used to determine the highest local temperature in the fixed catalyst bed and the position thereof in the fixed catalyst bed.

In each temperature zone, a heat exchange medium is conducted around the catalyst tubes between which the fixed catalyst bed has been divided. Preferred heat exchange media are melts of salts such as potassium nitrate, potassium nitrite, sodium nitrite and/or sodium nitrate, or of low-melting metals such as sodium, mercury and alloys of different metals.

The inlet temperature of the heat exchange medium is preferably set to 280° C. to 420° C., preferably to 300° C. to 400° C., more preferably to 320° C. to 380° C.

Viewed over the respective temperature zone, the heat exchange medium can be conducted in cocurrent or in countercurrent relative to the reaction gas mixture. The flow rate of the heat exchange medium within the respective temperature zone is generally selected such that the temperature of the heat exchange medium rises from the entry point into the temperature zone to the exit point from the temperature zone by 0 to 15° C., frequently 1 to 10° C., or 2 to 8° C., or 3 to 6° C. Within the temperature zone, the heat exchange medium is preferably conducted in a meandering manner.

The process can be started up, for example, as described in DE-A 103 37 788 or as described in DE-A 102009047291.

An α,β-unsaturated aldehyde prepared by the process according the invention can be converted further to the α,β-unsaturated carboxylic acid in a second stage.

By-production of α,β-unsaturated carboxylic acid (acrylic acid, methacrylic acid) accompanying the gas phase oxidation of alkene (propene, isobutene) to give α,β-unsaturated aldehyde (acrolein, methacrolein) is generally undesirable.

The products of value (aldehyde and carboxylic acid) can be separated in a later process step.

EXAMPLES

Preparation of Hollow Cylindrical Shaped Catalyst Bodies

Solution A: A temperature-controllable stainless steel vessel (capacity=5 dm³) which was open to the atmosphere (1 atm, 1.01 bar) and was equipped with an anchor stirrer was initially charged with 1060.5 g of an aqueous cobalt(II) nitrate solution (12.3% by weight of Co, 27% by weight of nitrate ($NO^{3-}$)), pH=1, prepared by dissolving cobalt metal from MFT Metals & Ferro-Alloys Trading GmbH, D-41474 Viersen, purity >99.6% by weight of Co, <0.3% by weight of Ni, <100 mg/kg of Fe, <50 mg/kg of Cu, in nitric acid), which was heated to 60° C. while stirring (150 rpm). While continuing to stir (150 rpm) and continuing to heat to 60° C., 225.0 g of crystalline iron(III) nitrate nonahydrate (13.9% by weight of Fe, <0.4% by weight of alkali metals, <0.01% by weight of chloride, <0.02% by weight of sulfate, from Dr. Paul Lohmann GmbH, D-81857 Emmerthal) were metered in and the mixture was stirred at 60° C. for a further 10 min. Added to the resulting aqueous solution were 278.6 g of an aqueous bismuth nitrate solution in nitric acid at 60° C. (12.0% by weight of Bi, 13% by weight of nitrate, prepared by dissolving bismuth metal from Sidech S. A., BE-1495 Tilly, purity >99.997% by weight of Bi, <7 mg/kg of Pb, <5 mg/kg each of Ni, Ag, Fe, <3 mg/kg each of Cu, Sb and <1 mg/kg of Cd, Zn in nitric acid), and the mixture was stirred at 60° C. for a further 10 min.

Solution B: A temperature-controllable stainless steel vessel (capacity=10 dm³) which was open to the atmosphere (1 atm, 1.01 bar) and was equipped with an anchor stirrer was initially charged with 4750 g of demineralized water and heated to 60° C. while stirring (150 rpm). Subsequently, 2.53 g of a 33% by weight aqueous solution of KOH in water at a temperature of 60° C. were added. After stirring at 60° C. for a further 1 minute, while keeping the mixture at 60° C., 568.53 g of ammonium heptamolybdate tetrahydrate (white crystals having a particle size d of <1 mm, 54% by weight of Mo, 7.0-8.5% by weight of $NH_3$, max. 150 mg/kg of alkali metals, from H. C. Starck, D-38642 Goslar) were stirred in in portions and the resulting aqueous solution was stirred (150 rpm) at 60° C. for a further 20 min.

Solution A at 60° C. was metered continuously with the aid of a peristaltic pump (model: BVP, supplier: Ismatec SA, Labortechnik-Analytik, Feldeggstrasse 6, CH-8152 Glattbrugg, setting: 320 scale divisions) into solution B which was at 60° C. and was now being stirred vigorously with an Ultra-Turrax (from Janke & Kunkel GmbH & Co. KG-IKA-Labortechnik, Janke & Kunkel-Str. 10, DE-79219 Staufen, shaft type: 550KR-G45 fein, shaft diameter: 25 mm, stator diameter: 45 mm, rotor diameter: 40 mm, setting: level 5) within 15 min. Solution A was introduced at the level of the rotor of the Ultra-Turrax stirrer, offset by about 0.5 to 1 cm from the outer edge of the rotor of the Ultra-Turrax stirrer. The resulting aqueous suspension was stirred at 60° C. for another 15 min.

The aqueous suspension was admixed with 48.5 g of Grace Ludox TM50 silica gel heated to 60° C. (24.4% by weight of Si, density: 1.29 g/cm³, pH: 8.5 to 9.5, alkali metal content max. 0.5% by weight), stirred at 60° C. for a further 15 min and then spray-dried in a Mobile Minor™ 2000 (MM-I) spray tower from Niro A/S, Gladsaxevej 305, 2860 Soborg, Denmark, with a centrifugal atomizer of the F01A type and an atomizer wheel of the SL24-50 type in a hot air cocurrent within 90 to 140 min (gas inlet temperature: 350+-10° C., gas outlet temperature: 140+-5° C.). The stirring of the fraction which was yet to be spray-dried was continued at a constant 60° C. The setting of the speed of the atomizer wheel was 25 000 rpm. In this way, about 942 g of orange-brown spray powder were obtained. The residual moisture content of the spray powder (residual moisture content determination by means of microwaves) was 3% by weight based on the total weight of the spray powder.

In a drum-hoop mixer (hoop diameter: 650 mm, drum volume: 5 l), based on the weight of the spray powder, 1% by weight of TIMREX T44 finely divided graphite from Timcal Ltd., CH-6743 Bodio (cf. WO 2008/087116) were mixed into the spray powder in homogeneous distribution (speed: 30 rpm, mixing time: 30 min). In a laboratory calender with 2 contra-rotating steel rollers (roller diameter: 10 cm; roller length utilized for intermediate compaction: 13.5 cm; roller speed: 10 rpm), the homogeneous mixture was compacted at a pressure of 9 bar and then forced through a screen having square meshes (edge length=0.8 mm). In the above-described drum-hoop mixer (30 rpm, mixing time 30 min), based on the weight of the coarsened spray powder, a further 2.5% by weight of the same finely divided graphite were mixed into the thus coarsened spray powder. Subsequently, the finely divided intimate dry mixture thus obtained, as described in DE-A 10200804093, was compacted (tableted) with a Kilian 5100 rotary tableting press (9-die tableting machine) (from Kilian, D-50735 Cologne) under a nitrogen atmosphere and at an ambient temperature of 25° C. to give hollow cylindrical shaped bodies of geometry ED×H×ID=5 mm×3 mm×2 mm. The settings of the tableting machine were such that the tablet weight was 119 mg, corresponding to a tablet density of 2.4 kg/l.

Shaped bodies of geometry ED×H×ID=5 mm×3 mm×2.5 mm, ED×H×ID=5 mm×3 mm×3 mm, ED×H×ID=6 mm×3 mm×2 mm, ED×H×ID=6 mm×3 mm×3 mm and ED×H×ID=4 mm×3 mm×2 mm were produced correspondingly. The control parameter in the adjustment of the tableting machine in each case was a target tablet density of 2.4 kg/l.

The thermal pretreatment and calcination of the shaped bodies thus obtained was effected as described on page 29 of DE 10 2011 084 040 A1 for annular shaped unsupported catalyst bodies.

Gas Phase Oxidation of Propene to Acrolein and Acrylic Acid Using a Fixed Catalyst Bed Having Successive Reaction Zones A reaction tube (1.4541 stainless steel (EU standards number EN 10088-3; external diameter 33.7 mm; wall thickness 2 mm; internal diameter 29.7 mm; length 400 cm, thermowell 4 mm) was charged from the bottom upward as follows:

Section 1: length 90 cm
  upstream bed of steatite rings of geometry 7 mm×3 mm×4 mm (external diameter×length×internal diameter; C220 steatite from CeramTec);
Reaction zone: consisting of 2-3 sections (see table 1; zone 1 is the closest to the reactor inlet)
Section 2: length 57 cm
  downstream bed of the same steatite rings as in section 1;
Section 3: length 46 cm
  empty tube Table 1 presents the structures of the reaction zones. To adjust relative volume-specific catalyst activity, shaped catalyst bodies were diluted with inert steatite rings of geometry 5 mm×3 mm×2 mm (external diameter×length×internal diameter, C220 steatite from CeramTec).

A reaction gas mixture having the following contents was conducted from the top downward through the respective reaction tube charged as described above:
5.2 to 6.5% by volume of propene,
3 to 3.5% by volume of $H_2O$,
0.3 to 0.6% by volume of CO,
0.6 to 1.0% by volume of $CO_2$,
0.02 to 0.05% by volume of acrolein,
9.8 to 10.4% by volume of $O_2$ and
as the remaining amount to 100% molecular nitrogen.

The space velocity of propene toward the fixed catalyst bed in each case was 100 l (STP)/(lh).

A stirred and externally electrically heated salt bath (mixture of 53% by weight of potassium nitrate, 40% by weight of sodium nitrite and 7% by weight of sodium nitrate; 50 kg of salt melt) flowed around each reaction tube over its length (the flow rate at the tube was 3 $m^3$/h (in the plane at right angles to the longitudinal axis of the tube)).

The salt bath temperature $T^B$ (° C.) (with which the salt bath was supplied) was set in all cases so as to result in a propene conversion, based on a single pass of the reaction gas mixture through the fixed catalyst bed, of 96.0 mol %. There was no change in the salt bath temperature along the reaction tube as a result of additional heating (more heat was emitted from the salt bath than was released from the reaction tube to the salt bath). The feed temperature of the reaction gas mixture (at the inlet into the reaction tube) was set to the respective salt bath temperature in each case.

The temperature in the catalyst bed was measured continuously by a thermocouple which had been positioned in a thermowell within the interior of the reactor tube and had been moved from the bottom upward within the reactor bed with the aid of a tractor machine. The maximum temperature of this measurement corresponded to the hotspot temperature $T^H$.

$$S = \frac{\text{number of moles of propene converted to acrolein and acrylic acid} \times 100}{\text{number of moles of propene converted overall}}$$

(the conversion numbers each based on a single pass of the reaction gas mixture through the fixed catalyst bed).

Gas Phase Oxidation of Propene to Acrolein and Acrylic Acid Using a Fixed Catalyst Bed with Two Successive Heating Zones A thermal reaction tube (V2A steel; external diameter 33.7 mm, wall thickness 2 mm, internal diameter 29.7 mm, length: 350 cm, and a thermal protection tube (thermowell) running through the center of the thermal tube from the top downward for accommodating a thermocouple with which the reaction temperature (the effective fixed catalyst bed temperature) was determinable over the entire tube length) was charged from the top downward as follows:

Section 1: length 50 cm
    steatite rings of geometry 7 mm×7 mm×4 mm (external diameter×length×internal diameter, C220 steatite from CeramTec) as a preliminary bed.

Section 2 length 10 cm
    catalyst charge with a homogeneous mixture consisting of 20% by weight of steatite rings of geometry 5 mm×3 mm×2 mm (external diameter×length×internal diameter; C220 steatite from CeramTec), 80% by weight of shaped catalyst bodies of geometry ED×H×ID=5 mm×3 mm×2 mm.

Section 3 length 130 cm
    catalyst charge with a homogeneous mixture consisting of 20% by weight of steatite rings of geometry 5 mm×3 mm×2 mm (external diameter×length×internal diam-

TABLE 1

| | Reaction zone: length [m] | | | Shaped catalyst bodies: dimensions [mm] ($ED^{1)} \times H^{2)} \times ID^{3)}$) | | | Dilution with inert material [% by weight] | | | Relative volume-specific catalyst activity [%] | | |
|---|---|---|---|---|---|---|---|---|---|---|---|---|
| Ex. | Zone 1 | Zone 2 | Zone 3 | Zone 1 | Zone 2 | Zone 3 | Zone 1 | Zone 2 | Zone 3 | Zone 1 | Zone 2 | Zone 3 |
| 1 | 0.1 | 0.9 | 1.8 | 5 × 3 × 2 | 5 × 3 × 3 | 5 × 3 × 2 | 20 | 20 | 0 | 80 | 56 | 100 |
| 2 | 0.1 | 0.9 | 1.8 | 5 × 3 × 2 | 5 × 3 × 3 | 5 × 2 × 2 | 20 | 20 | 0 | 80 | 56 | 100 |
| 3*) | 0.1 | 0.9 | 1.8 | 5 × 3 × 2 | 5 × 3 × 2 | 5 × 3 × 2 | 20 | 40 | 0 | 80 | 60 | 100 |
| 4*) | 1 | 1.8 | | 5 × 3 × 2 | 5 × 3 × 2 | — | 40 | 0 | — | 60 | 100 | |
| 5 | 0.1 | 0.9 | 1.8 | 5 × 3 × 2 | 4 × 3 × 2 | 5 × 3 × 2 | 20 | 40 | 0 | 80 | 60 | 100 |

*)comparative example
1)external diameter
2)height
3)internal diameter

TABLE 2

| Ex. | $T^{B\ 1)}$ (° C.) | $T^{H\ 2)}$ (° C.) | $y^{H\ 3)}$ (m) | $S^{\ 4)}$ (mol %) |
|---|---|---|---|---|
| 2 | 346 | 405 | 0.4 | 96.65 |
| 3*) | 346 | 396 | 0.35 | 96.3 |

1) salt bath temperature
2) hotspot temperature
3) hotspot position (the zero point is the start of the reaction zone); the position 0.4 or 0.35 shows that the hotspot in both cases is in the 2nd zone.
4) selectivity of product of value formation (products of value: acrolein and acrylic acid) based on the propene converted The selectivity of product of value formation (S (mol %)) is understood in this document to mean:

eter; C220 steatite from CeramTec), 80% by weight of shaped catalyst bodies of geometry ED×H×ID=5 mm×3 mm×3 mm.

Section 4: length 160 cm
    catalyst charge of 100% by weight of shaped catalyst bodies of geometry ED×H×ID=5 mm×3 mm×2 mm.

The thermal reaction tube is supposed to reflect the behavior of a simple reaction tube made of corresponding material with identical tube length, the internal diameter of which is 26 mm with wall thickness 2 mm, and which is charged in a corresponding manner to the thermal reaction tube.

From the top downward, the first 175 cm of the thermal reaction tube were thermostatted by means of a salt bath A pumped in countercurrent to the reaction mixture over the 175 cm, which was supplied with the temperature T_A. The second 175 were thermostatted by means of a salt bath B pumped in countercurrent in a corresponding manner, which was supplied with the temperature T_B. Over the particular temperature zone, the particular salt bath temperature was essentially constant.

The two salt baths A, B each consisted of 53% by weight of potassium nitrate, 40% by weight of sodium nitrite and 7% by weight of sodium nitrate. In the two tube sections, each of length 175 cm, the flow toward the reaction tube was essentially vertical with respect to the flow direction of the reaction gas. The flow rate of the two salt melts was such that a further increase essentially did not bring about any improvement in the heat transfer from the thermal tube interior into the salt bath (cf. EP-A1547994).

The thermal tube charged as described above was charged with a reaction gas input mixture which had the following contents and was obtained from air (as the oxygen source), chemical-grade propene and cycle gas:

6 to 6.5% by vol. of propene
0.7 to 1.2% by vol. of $H_2O$,
0.4 to 0.6% by vol. of CO,
0.7 to 1.1% by vol. of $CO_2$,
0.01 to 0.04% by vol. of acrolein,
0.005 to 0.015% by vol. of ethene,
0.025 to 0.035% by vol. of propane,
10.8 to 11.7% by vol. of $O_2$ and
at least 77% by vol. of $N_2$.

The space velocity of propene present in the reaction gas input mixture on the fixed catalyst bed was always within the range of 150 to 200 l (STP)/(lh). The pressure at the inlet of the thermal reaction tube was within the range of 1.5 to 2.5 barG. The temperatures T_A and T_B were 325 and 341° C., respectively.

The invention claimed is:

1. A process for preparing an α,β-unsaturated aldehyde and/or an α,β-unsaturated carboxylic acid, the process comprising:

reacting an alkene with molecular oxygen by gas phase oxidation in a reactor with an inlet and an outlet over a fixed catalyst bed comprising a bed of hollow cylindrical shaped catalyst bodies comprising a multimetal oxide active composition, wherein the fixed catalyst bed comprises at least three successive reaction zones;

the highest local temperature in the fixed catalyst bed does not occur in a reaction zone closest to the reactor outlet;

the highest local temperature in the fixed catalyst bed does not occur in a reaction zone closest to the reactor inlet; and a value WT calculated according to the following equation in a reaction zone in which the highest local temperature in the fixed catalyst bed occurs is lower than WT values in the other reaction zones:

$$WT = \frac{ED - ID}{2}$$

where ED is an external diameter and ID is an internal diameter of the cylindrical shaped catalyst body.

2. The process according to claim 1, wherein the multimetal oxide active composition comprises iron, bismuth and at least one of molybdenum and tungsten.

3. The process according to claim 2, wherein the multimetal oxide active composition corresponds to formula (I)

$$Mo_{12}Bi_aFe_bX^1_cX^2_dX^3_eX^4_fO_n \quad (I)$$

where
$X^1$ is nickel and/or cobalt,
$X^2$ is thallium, an alkali metal and/or an alkaline earth metal,
$X^3$ is zinc, phosphorus, arsenic, boron, antimony, tin, cerium, lead, vanadium, chromium and/or tungsten,
$X^4$ is silicon, aluminum, titanium and/or zirconium,
a is a number of from 0.2 to 5,
b is a number of from 0.01 to 10,
c is a number of from 0 to 10,
d is a number of from 0 to 2,
e is a number of from 0 to 8,
f is a number of from 0 to 10, and
n is a number determined by valency and frequency of elements other than oxygen in the formula (I);
or the multimetal oxide active composition corresponds to formula (II)

$$[Y^1_aY^2_bO^{x'}]_p[Y^3_{c'}Y^4_{d'}Y^5_{e'}Y^6_{f'}Y^7_{g'}Y^8_{h'}O_{y'}]_q \quad (II)$$

where
$Y^1$ is bismuth or is bismuth and at least one of tellurium, antimony, tin and copper,
$Y_2$ is molybdenum or tungsten, or is molybdenum and tungsten,
$Y^3$ is an alkali metal, thallium and/or samarium,
$Y^4$ is an alkaline earth metal, nickel, cobalt, manganese, zinc, tin, cadmium and/or mercury,
$Y^5$ is iron or is iron and at least one of vanadium, chromium and cerium,
$Y^6$ is phosphorus, arsenic, boron, antimony and/or bismuth,
$Y^7$ is a rare earth metal, titanium, zirconium, niobium, tantalum, rhenium, ruthenium, rhodium, copper, silver, gold, aluminum, gallium, indium, silicon, germanium, lead, thorium and/or uranium,
$Y^8$ is molybdenum or tungsten, or is molybdenum and tungsten,
a' is a number of from 0.01 to 8,
b' is a number of from 0.1 to 30,
c' is a number of from 0 to 4,
d' is a number of from 0 to 20,
e' is a number greater than 0 to but not greater than 20,
f' is a number of from 0 to 6,
g' is a number of from 0 to 15,
h' is a number of from 8 to 16,
x' and y' are numbers determined by valency and frequency of elements other than oxygen in the formula (II), and
p and q are numbers whose ratio p/q is from 0.1 to 10.

4. The process according to claim 1, wherein the cylindrical shaped catalyst bodies have a geometric volume of less than 80 mm³.

5. The process according to claim 1, wherein a volume-specific catalyst activity of the reaction zone in which the highest local temperature in the fixed catalyst bed occurs is lower than volume-specific catalyst activity in the other reaction zones.

6. The process according to claim 1, wherein a catalyst active composition density in the reaction zone in which the highest local temperature in the fixed catalyst bed occurs is lower than catalyst active composition densities in the other reaction zones.

7. The process according to claim 1, wherein the cylindrical shaped catalyst bodies have a density of from 1.2 to 2.0 g/cm³.

8. The process according to claim 1, wherein
the external diameter of the cylindrical shaped catalyst bodies in the reaction zone in which the highest local temperature in the fixed catalyst bed occurs is less than the external diameter of the cylindrical shaped catalyst bodies in the other reaction zones, and
the internal diameter of the cylindrical shaped catalyst bodies in all the reaction zones is the same.

9. The process according to claim 1, wherein
the internal diameter of the cylindrical shaped catalyst bodies in the reaction zone in which the highest local temperature in the fixed catalyst bed occurs is greater than the internal diameter of the cylindrical shaped catalyst bodies in the other reaction zones, and
the external diameter of the cylindrical shaped catalyst bodies in all the reaction zones is the same.

10. The process according to claim 1, wherein the cylindrical shaped catalyst bodies in all reaction zones have the same height.

11. The process according to claim 1, wherein the fixed catalyst bed comprises a first, a second, and a third successive reaction zones, and
the first reaction zone makes up 2 to 5% by volume of the fixed catalyst bed,
the second reaction zone makes up 25 to 45% by volume of the fixed catalyst bed, and
the third reaction zone makes up 50 to 73% by volume of the fixed catalyst bed.

12. The process according to claim 1, wherein the fixed catalyst bed comprises a first, a second, and a third successive reaction zones, and
the first reaction zone has 70 to 90% of volume-specific catalyst activity of the third reaction zone, and
the second reaction zone has 50 to 70% of the volume-specific catalyst activity of the third reaction zone.

13. The process according to claim 1, wherein the fixed catalyst bed comprises a first, a second, and a third successive reaction zones, and
the first reaction zone has 70 to 90% of catalyst active composition density of the third reaction zone, and
the second reaction zone has 50 to 70% of the catalyst active composition density of the third reaction zone.

14. The process according to claim 1, wherein the cylindrical shaped catalyst bodies have an external diameter of from 3 to 5 mm, a height of from 2 to 4 mm, and an internal diameter of from 1 to 4 mm.

15. The process according to claim 1, wherein the fixed catalyst bed comprises a first, a second, and a third successive reaction zones, and
the first reaction zone comprises shaped catalyst bodies having an external diameter of 5 mm, a height of 3 mm and an internal diameter of 2 mm,
the second reaction zone comprises shaped catalyst bodies having an external diameter of 5 mm, a height of 3 mm and an internal diameter of 3 mm, and
the third reaction zone comprises shaped catalyst bodies having an external diameter of 5 mm, a height of 3 mm and an internal diameter of 2 mm.

16. The process according to claim 1, wherein the fixed catalyst bed comprises a first, a second, and a third successive reaction zones, and
the first reaction zone comprises shaped catalyst bodies having an external diameter of 5 mm, a height of 2.5 mm and an internal diameter of 2 mm,
the second reaction zone comprises shaped catalyst bodies having an external diameter of 5 mm, a height of 2.5 mm and an internal diameter of 3 mm, and
the third reaction zone comprises shaped catalyst bodies having an external diameter of 5 mm, a height of 2.5 mm and an internal diameter of 2 mm.

17. The process according to claim 1, wherein the fixed catalyst bed comprises a first, a second, and a third successive reaction zones, and
the first reaction zone comprises shaped catalyst bodies having an external diameter of 5 mm, a height of 3 mm and an internal diameter of 2 mm,
the second reaction zone comprises shaped catalyst bodies having an external diameter of 4 mm, a height of 3 mm and an internal diameter of 2 mm, and
the third reaction zone comprises shaped catalyst bodies having an external diameter of 5 mm, a height of 3 mm and an internal diameter of 2 mm.

18. The process according to claim 1, wherein the fixed catalyst bed comprises a first, a second, and a third successive reaction zones, and
the first reaction zone comprises shaped catalyst bodies having an external diameter of 5 mm, a height of 2.5 mm and an internal diameter of 2 mm,
the second reaction zone comprises shaped catalyst bodies having an external diameter of 4 mm, a height of 2.5 mm and an internal diameter of 2 mm, and
the third reaction zone comprises shaped catalyst bodies having an external diameter of 5 mm, a height of 2.5 mm and an internal diameter of 2 mm.

19. The process according to claim 1, wherein one or more reaction zones in the fixed catalyst bed comprise mixtures of shaped catalyst bodies and inert material.

20. The process according to claim 19, wherein the inert material is in a form of hollow cylindrical shaped bodies, which has dimensions corresponding essentially to the external diameter, height and internal diameter of the shaped catalyst bodies in the respective reaction zone.

21. The process according to claim 19, wherein steatite is the inert material.

22. The process according to claim 1, wherein
the alkene is propene, and
the α,β-unsaturated aldehyde is acrolein.

* * * * *